United States Patent [19]

Imanari et al.

[11] Patent Number: 4,568,778

[45] Date of Patent: Feb. 4, 1986

[54] PROCESS FOR PRODUCING TERT-AMYLPHENOLS

[75] Inventors: Makoto Imanari; Hiroshi Iwane; Takahiro Sugawara; Tadashi Ayusawa; Tadamichi Aoki, all of Ibaraki, Japan

[73] Assignee: Mitsubishi Petrochemical Co., Ltd., Tokyo, Japan

[21] Appl. No.: 699,130

[22] Filed: Feb. 7, 1985

[30] Foreign Application Priority Data

Feb. 20, 1984 [JP] Japan ................................. 59-28800

[51] Int. Cl.$^4$ ............................................. C07C 37/14
[52] U.S. Cl. .................................. 568/789; 568/784; 568/785
[58] Field of Search ................. 568/784, 788, 789, 785

[56] References Cited

U.S. PATENT DOCUMENTS

Re. 23,183 12/1949 Arvin et al. ........................ 568/786

FOREIGN PATENT DOCUMENTS 1156082 10/1968 Fed. Rep. of Germany ...... 568/786
144854 2/1962 U.S.S.R. .............................. 568/786
292942 4/1971 U.S.S.R. .............................. 568/788

Primary Examiner—Werren B. Lone
Attorney, Agent, or Firm—Oblon, Fisher, Spivak, McClelland & Maier

[57] ABSTRACT

A process for producing tert-amylphenols is described, comprising reacting isoamylene with phenols in the presence of an inorganic solid acid catalyst or an acidic ion exchange resin catalyst. This process permits efficient production of tert-amylphenols, i.e., 2,4-di-tert-amylphenol and p-tert-amylphenol. These tert-amylphenols are useful as starting materials for preparation of color formers for color photography, additives for resins, oil-soluble dyes, additives for lubricating oils, etc.

9 Claims, No Drawings

PROCESS FOR PRODUCING TERT-AMYLPHENOLS

FIELD OF THE INVENTION

The present invention relates to a process for producing tert-amylphenols. More particularly, it is concerned with a process for producing useful tert-amylphenols in good yields by reacting isoamylene and phenols in the presence of a specific catalyst.

The term "tert amylphenols" as used herein means both 2,4-di tert-amylphenol and p-tert-amylphenol.

BACKGROUND OF THE INVENTION

In the production of tert-amylphenols, o-tertamylphenol is by-produced. Although this o-tert-amylphenol can be used as a starting material for the production of 2,4-di-tert-amylphenol, it is difficult to separate it from p-tert-amylphenol. It is therefore preferred that byproduction of o-tert-amylphenol be reduced. 2,4,6-Tri-tertamylphenol has no value as a product and, therefore, it is desirable that the amount of 2,4,6-tri-tert-amylphenol formed be minimized as less as possible.

In recent years, 2,4-di-tert-amylphenol has been used, for example, as a starting material for the production of color formers for color photography and also additives for resins, and p-tert-amylphenols has been used, for example, as a starting material for oil-soluble dye intermediates and additives for lubricating oils.

High purity 2,4-di-tert-amylphenol or p-tertamylphenol is required in the above-described uses. In conventional methods, therefore, high purity isoamylene or tert-amyl alcohol is reacted with phenol to prepare the desired products. However, isoamylene and tert-amyl alcohol are expensive and are not readily available.

In order to overcome the above problem, a method has been proposed in which tert-amylphenols are produced from isoamylene contained in a C5 fraction from which isoprene had been extracted (see Japanese Patent Application (OPI) No. 35122/75 (the term "OPI" as used herein means a "published unexamined Japanese patent application")). In accordance with this method, after removal of isoprene and cyclopentadiene from the C5 fraction with maleic anhydride, the resulting C5 fraction is reacted with phenols in the presence of, for example, organic carboxylic anhydrides using sulfuric acid as a catalyst to produce tert-amylphenols.

This method, however, has several disadvantages. One of the disadvantages is that the yield of 2,4-di-tertamylphenol is low and the amount of o-tert-amylphenol by-produced which has no value reaches about 20%. Another disadvantage is that a neutralization/separation process is required due to the use of sulfuric acid as a catalyst. Moreover, in this method, the dienes contained in the C5 fraction are removed using maleic anhydride. This method takes a time as long as 16 hours until the reaction is completed.

SUMMARY OF THE INVENTION

As a result of extensive investigations to overcome the above-described problems of the prior art, it has been found that the problems can be overcome and the desired result can be obtained by using an inorganic solid acid and acidic ion exchange resin as a catalyst.

Accordingly, an object of the present invention is to provide a process for producing tert-amylphenols comprising reacting isoamylene with phenols in the presence of a catalyst selected from the group consisting of an inorganic solid acid and an acidic ion exchange resin.

DETAILED DESCRIPTION OF THE INVENTION

The term "isoamylene" as used herein means 2-methyl-1-butene and 2-methyl-2-butene and those can be used alone or as a mixture thereof. It is preferred for this isoamylene to be diluted with hydrocarbons as described hereinafter in that the amount of o-tert-amyl-phenol formed is decreased.

Hydrocarbons which can be used to dilute the isoamylene are hydrocarbons which do not include olefins represented by the following formula (I) and/or dienes.

Olefins which cannot be used to dilute the isoamylene are represented by the formula (I):

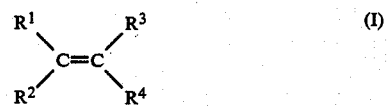

wherein $R^1$ and $R^2$ each is an alkyl group having from 1 to 6 carbon atoms, and $R^3$ and $R^4$ each is an alkyl group having from 1 to 6 carbon atoms or a hydrogen atom.

A representative example of isoamylene diluted with hydrocarbons which do not include the olefins of the formula (I) and/or dienes is one obtained by hydrogenating an isoprene-extracted C5 fraction which is used in a large amount in petrochemical industries in the presence of conventional transition metal-based hydrogenation catalysts such as palladium and nickel thereby to convert dienes therein into the corresponding monolefins.

The inorganic solid acid catalyst which can be used in the present invention has an acid strength $H_0$ of $-3$ or less. This acid strength $H_0$ indicates an ability of an acid site on the surface of the solid acid to give a proton to a base, or to receive an electron pair therefrom, and is determined using various acid-base conversion indicators having the known pKa (see K. Tanabe & T. Takeshita, *Acid Base Catalysts,* published by Sangyo Tosho Co., Ltd., pp. 161–162 (1966)).

Examples of the inorganic solid acid catalysts having an acid strength of $-3$ or less include composite oxides such as silica-alumina, various zeolites, titania-silica, titania-zirconia, and magnesia-silica; clay minerals such as activated clay, bentonite, and kaolin; mounted acids prepared by depositing sulfuric acid or phosphoric acid, for example, on silica gel or alumina; fixed compounds such as metal sulfates, metal phosphates, and metal halides; and heteropolyacid.

In addition to the above-described inorganic solid acid catalysts, inorganic solid acid catalysts having an acid strength $H_0$ of $-3$ or less as described in the above-described reference, "*Acid Base Catalyst*", page 160, and also T. Shimizu, *Metal Oxide and Its Catalytic Action,* published by Kodan Sha Co., Ltd., page 103 (1978) can be used.

Of these inorganic solid acid catalysts, composite oxides such as silica-alumina, zeolite, titania-silica, and titania-zirconia, and clay minerals such as activated clay are preferred.

The solid acid catalyst can be easily separated from the reaction product by techniques such as filtration. Moreover, the solid acid catalyst does not produce at all alkylphenols resulting from the reaction of olefins other than isoamylene contained in the isoprene-extracted $C_5$ fraction which has been hydrogenated, with phenols.

In addition to the inorganic solid acid catalyst, an acidic ion exchange resin can be used as the catalyst of the present invention.

As such acidic ion exchange resin catalysts, strongly acidic sulfonic acid-type ion exchange resins can be used. If these ion exchange resins contain water, the resins must be heated to about 100° C. and vacuum dried prior to use. Of course, if the water content is 1% by weight or less, the ion exchange resin catalyst can be used without removal of water. Representative examples of such ion exchange resins are Amberlist 15, Amberlite XN-1010 (produced by Rohm & Haas Co., Ltd.), Dowex 50 W, Dowex 50 W-X4 (produced by Dow Chemical Co., Ltd.), and Diaion SK116, Diaion SK1B (produced by Mitsubishi Chemical Industries Limited).

As the catalyst used in the process of the present invention, the inorganic solid acid catalyst is preferred as compared to the acidic ion exchange resin catalyst in that the amounts of 2,4,6-tri-tert-amylphenol and o-tertamylphenol formed are small.

Phenols which can be used in the process of the present invention include phenol, o-, p- or m-cresol, 2,3-, 2,4- or 2,6-xylenol, 2,3-, 2,4- or 2,6-dihalogenated phenol, 2-methyl-4-tert-butylphenol, 2-isobutyl-6-dodecylphenol, 2-cyclohexyl-6-methylphenol, 2,3,6-trimethylphenol, and 2,3,5,6-tetramethylphenol.

In accordance with the process of the present invention, the above-described isoamylene is reacted with phenols in the presence of the inorganic solid acid catalyst or acidic ion exchange resin to produce tert-amylphenols. This reaction is usual,ly carried out at a temperature ranging between 30° and 120° C. under a pressure ranging between 1 to 10 kg/cm² for from 1 to 7 hours.

The reaction can be carried out batchwise. For example, 1.0 kg of phenol, from 0.2 to 5 kg, preferably from 0.5 to 2 kg of a catalyst, and a hydrogenated isoprene-extracted $C_5$ fraction containing from 1 to 8 moles, preferably from 2 to 4 moles, per mole of phenol of isoamylene are placed an an autoclave and then reacted with stirring at a temperature of from 30° to 120° C., preferably from 50° to 80° C., for from 1 to 7 hours, preferably from 2 to 5 hours.

After the reaction is completed, the catalyst is removed from the reaction mixture by filtration and the major portion of the unreacted $C_5$ fraction is removed. The thus-obtained concentrate is distilled to separate and purify the desired product, tert-amylphenol.

In accordance with the process of the present invention, when the above-described hydrogenated isopreneextracted $C_5$ fraction is used, only isoamylene contained therein can be reacted with phenols, so that p-tert-amylphenol and 2,4-di-tert-amylphenol can be produced selectively. Thus, high purity tert-amylphenols can be produced inexpensively.

The present invention is described in greater detail by reference to the following non-limiting Examples and Comparative Example. Unless otherwise indicated, all percents, parts, ratios and the like are by mol.

EXAMPLE 1

Hydrogenation of Isoprene-Extracted $C_5$ Fraction

A mixture of 400 g of an isoprene-extracted $C_5$ fraction having a composition shown in Table 1 below and 4.0 g of a 0.3% palladium/alumina catalyst was placed in a 1.0-liter SUS autoclave and the autoclave was then closed. Hydrogen was charged to the autoclave at a gauge pressure of 5.0 kg/cm², and hydrogenation was conducted with stirring at 85° C. for 1.0 hour. After the reaction was completed, hydrogen was withdrawn, and the catalyst was removed by filtration to obtain a hydrogenated $C_5$ fraction. The composition of the $C_5$ fraction thus obtained is shown in Table 2 below.

TABLE 1

|  | Amount (%) |
|---|---|
| Isopentane | 31.3 |
| n-Pentane | 33.4 |
| 1-Pentene | 7.0 |
| Trans-2-pentene | 2.4 |
| Cis-2-pentene | 1.2 |
| 2-Methyl-1-butene | 10.0 |
| 2-Methyl-2-butene | 1.4 |
| Isoprene | 0.9 |
| Piperylene | 4.7 |
| Other compounds | 7.7 |

TABLE 2

|  | Amount (%) |
|---|---|
| Isoprene | 28.6 |
| n-Pentane | 34.6 |
| 1-Pentene | 1.8 |
| Trans-2-pentene | 9.2 |
| Cis-2-pentene | 3.4 |
| 2-Methyl-1-butene | 7.9 |
| 2-Methyl-2-butene | 5.2 |
| Isoprene | 0 |
| Piperylene | 0 |
| Cyclopentane | 0.2 |
| Other compounds | 9.1 |

Preparation of Tert-Amylphenols

A 50 ml autoclave was charged with 0.91 g (9.64 millimoles) of phenol, 10.3 g of the $C_5$ fraction as prepared above, and 1.00 g of Activated Clay (Strong) (produced by Nippon Kassei Hakudo Co., Ltd.) which had been burned at 200° C. for 6 hours, and the autoclave was then closed. The acid strength of the activated clay (as determined using a Hammet indicator) was as follows: $-5.6 < H_0 \leq -3.6$. The closed autoclave was maintained at 70° C. for 3 hours while stirring at about 800 rpm to conduct a reaction. The gauge pressure, therein was 2.0 kg/cm². After the reaction was completed, the reaction mixture was cooled to room temperature, and the activated clay was removed by filtration. Gas chromatographic analysis according to the internal standard method showed that the proportion of the unreacted phenol was 1.1%, and 0.08 g (5.1%) of o-tert-amylphenol, 0.40 g (25.3%) of p-tert amylphenol, and 1.54 g (68.2%) of 2,4-di-tert-amylphenol were formed. The structure of each compound was confirmed by NMR, IR, and Mass spectral analyses.

EXAMPLE 2

The procedure of Example 1 was repeated except that 1.00 g (10.6 millimoles) of phenol, 11.4 g of the same $C_5$ fraction as used in Example 1, and 1.00 g of Silica-Alumina "IS-28" (produced by Shokubai Kasei Kogyo Co., Ltd.) which had been burned at 500° C. for 10 hours were used. The acid strength of the silica alumina (as determined in the same manner as in Example 1) was as follows: $H_0 \leq -8.2$. The proportion of the unreacted phenol was 5.0%, and 0.05 g (2.9%) of o-tert-amylphenol, 0.22 g (12.6%) of p-tertamylphenol, 1.73 g (69.6%) of 2,4-di-tert-amylphenol, and 0.01 g (0.3%) of 2,4,6-tri-tert-amylphenol were formed.

COMPARATIVE EXAMPLE 1

The procedure of Example 1 was repeated except that 1.04 g (11.1 millimoles) of phenol, 11.8 g of the same C$_5$ fraction as used in Example 1, and 1.00 g of the same silica-alumina as used in Example 2 but which had not been burned were used. Tert-amylphenols were not formed at all, and only the starting material, phenol, was recovered. The acid strength of the silica-alumina (as determined in the same manner as in Example 1) was as follows: $-3.0 < H_0 \leq +1.5$.

EXAMPLE 3

A 50 ml glass autoclave was charged with 1.14 g (12.1 millimoles) of phenol, 12.9 g of the same C$_5$ fraction as used in Example 1, and 1.00 g of Amberlist 15, and the autoclave was then closed and maintained at 40° C. for 3 hours while stirring at about 800 rpm. The gauge pressure therein was 1.0 kg/cm$^2$. The reaction mixture was analyzed in the same manner as in Example 1. 100% of the phenol was converted, and 0.21 g (10.7%) of o-tert-amylphenol, 0.59 (29.4%) of p-tert-amylphenol, 1.45 g (51.7%) of 2,4-di-tertamylphenol, and 0.13 g (3.5%) of 2,4,6-tri-tert-amylphenol were formed.

While the invention has been described in detail and with reference to specific embodiments thereof, it will be apparent to one skilled in the art that various changes and modifications can be made therein without departing from the spirit and scope thereof.

What is claimed is:

1. A process for producing 2,4-di-tert-amylphenol and p-tert-amylphenol which comprises reacting isoamylene with phenols in the presence of an inorganic solid acid catalyst selected from the group consisting of silica-alumina, zeolites, titania-silica, titania-zirconia and magnesia-silica and clay minerals selected from the group consisting of bentonite, activated clay and kaolin at elevated temperature and pressure.

2. The process of claim 1, wherein the isoamylene is selected from the group consisting of 2-methyl-1-butene, 2-methyl-2-butene and a mixture thereof.

3. The process of claim 1, wherein the isoamylene is diluted with hydrocarbons.

4. The process of claim 3, wherein the hydrocarbons are hydrocarbons which do not include olefins represented by the following formula and/or dienes

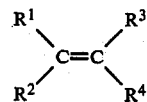

wherein R$^1$ and R$^2$ each is a C$_1$–C$_6$ alkyl group, and R$^3$ and R$^4$ each is a C$_1$–C$_6$ alkyl group or a hydrogen atom.

5. The process of claim 3 wherein the isoamylene diluted with hydrocarbons is one obtained by hydrogenating an isoprene-extracted C$_5$ fraction in the presence of transition metal-based hydrogenation catalysts to convert the dienes contained therein to the corresponding monoolefins.

6. The process of claim 1, wherein the phenols are selected from the group consisting of phenol, o-, m- or p-cresol, 2,3-, 2,4- or 2,6-xylenol, 2,3-, 2,4- or 2,6-dihalogenated phenol, 2-ethylphenol, 2,4- or 2,6-di-tert-butylphenol, 2-methyl-4-tert-butylphenol, 2-isobutyl-6-dodecylphenol, 2-cyclohexyl-6-methylphenol, 2,3,6-trimethylphenol and 2,3,5,6-tetramethylphenol.

7. The process of claim 1, wherein the reaction is conducted at a temperature of 30° to 120° C. and a pressure of 1 to 10 kg/cm$^2$ for 1 to 7 hours.

8. The process of claim 1, wherein the amount of the isoamylene is 1 to 8 mole per mol of the phenols.

9. The process of claim 1, wherein the amount of the catalyst is 0.2 to 5 kg per kg of the phenols.

* * * * *